(12) United States Patent
Plott et al.

(10) Patent No.: US 10,842,493 B2
(45) Date of Patent: Nov. 24, 2020

(54) DEVICE TO AID IN ARTERIAL MICROVASCULAR ANASTOMOSIS

(71) Applicant: THE REGENTS OF THE UNIVERSITY OF MICHIGAN, Ann Arbor, MI (US)

(72) Inventors: Jeffrey Stephen Plott, Algonac, MI (US); Paul S. Cederna, Ann Arbor, MI (US); Kirsten Boelkins, Ada, MI (US); Jeffrey H. Kozlow, Ann Arbor, MI (US); Jonathan William Zwier, Grand Rapids, MI (US); Krishna Mahajan, Minneapolis, MN (US); Kelsey L. Luibrand, Clarkston, MI (US); Martin Sisolak, Plymouth, MI (US); Sebastian Kwon, Okemos, MI (US); Aaron S. Farberg, Wilmette, IL (US); Adeyiza Momoh, Ann Arbor, MI (US); Albert J. Shih, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 315 days.

(21) Appl. No.: 15/755,506

(22) PCT Filed: Sep. 2, 2016

(86) PCT No.: PCT/US2016/050037
§ 371 (c)(1),
(2) Date: Feb. 26, 2018

(87) PCT Pub. No.: WO2017/040884
PCT Pub. Date: Mar. 9, 2017

(65) Prior Publication Data
US 2018/0271529 A1    Sep. 27, 2018

Related U.S. Application Data

(60) Provisional application No. 62/214,615, filed on Sep. 4, 2015.

(51) Int. Cl.
*A61B 17/11* (2006.01)
*A61M 25/10* (2013.01)
(Continued)

(52) U.S. Cl.
CPC ............. *A61B 17/11* (2013.01); *A61M 25/10* (2013.01); *A61B 2017/00345* (2013.01);
(Continued)

(58) Field of Classification Search
CPC ...... A61B 17/04; A61B 17/11; A61B 17/1114; A61B 17/1128; A61B 2017/1121;
(Continued)

(56) References Cited

U.S. PATENT DOCUMENTS

| 4,470,415 A | 9/1984 | Wozniak |
| 6,547,799 B2 | 4/2003 | Hess et al. |

(Continued)

FOREIGN PATENT DOCUMENTS

| CN | 1219856 A | 6/1999 |
| CN | 102202586 A | 9/2011 |

(Continued)

OTHER PUBLICATIONS

European Patent Application No. 16843041.1, Extended European Search Report, dated May 13, 2019.
(Continued)

*Primary Examiner* — Melanie R Tyson
(74) *Attorney, Agent, or Firm* — Marshall, Gerstein & Borun LLP

(57) ABSTRACT

An everter device to facilitate preparation of ends of arterial segments for end-to-end microvascular anastomosis. The
(Continued)

device includes structure that provides sufficient support to prevent unwanted buckling of arterial tissue. The everter device offsets the tendency of the arterial tissue wall to recover its natural shape and fall off securement posts or pins of a coupler ring. The structure may be in the form of an intraluminal catheter balloon. Alternately, the structure may be in the form of a plunger. Alternately, the structure may be in the form of a radially expanding member provided on a shaft. The device further has a contoured surface on an everter end to evert a free end of arterial tissue over a coupler ring, and to cause the posts or pins of the coupler ring to pierce through the everted arterial tissue. The everter end is provided with one or more openings therein, such as a circumferential slot, to receive the posts or pins of the coupler ring.

7 Claims, 18 Drawing Sheets

(51) Int. Cl.
*A61B 17/00* (2006.01)
*A61B 17/064* (2006.01)
*A61B 17/22* (2006.01)
*A61M 25/00* (2006.01)

(52) U.S. Cl.
CPC .............. *A61B 2017/00557* (2013.01); *A61B 2017/00946* (2013.01); *A61B 2017/0641* (2013.01); *A61B 2017/1107* (2013.01); *A61B 2017/1121* (2013.01); *A61B 2017/1132* (2013.01); *A61B 2017/22069* (2013.01); *A61M 2025/0042* (2013.01)

(58) Field of Classification Search
CPC .... A61B 2017/1107; A61B 2017/1132; A61B 2017/1135; A61B 2017/1139; A61B 2017/1146
See application file for complete search history.

(56) References Cited

U.S. PATENT DOCUMENTS

| | | |
|---|---|---|
| 6,740,101 B2 | 5/2004 | Houser et al. |
| 6,955,679 B1 | 10/2005 | Hendricksen et al. |
| 2002/0173808 A1 | 11/2002 | Houser et al. |
| 2002/0198545 A1 | 12/2002 | Hess et al. |
| 2003/0050651 A1 | 3/2003 | Knight et al. |
| 2003/0208214 A1* | 11/2003 | Loshakove ........ A61B 17/0644 606/153 |
| 2006/0085017 A1 | 4/2006 | Borghi |
| 2008/0269784 A1 | 10/2008 | Abbott et al. |
| 2010/0241148 A1 | 9/2010 | Schon et al. |

FOREIGN PATENT DOCUMENTS

| | | |
|---|---|---|
| WO | WO-01/70119 A1 | 9/2001 |
| WO | WO-2011/130656 A2 | 10/2011 |

OTHER PUBLICATIONS

Singapore Search Report and Written Opinion for Application No. 11201801693P, dated Apr. 4, 2019.
International Application No. PCT/US2016/050037, International Search Report and Written Opinion, dated Dec. 8, 2016.
Chinese Patent Application No. 201680050903.8, First Office Action, dated May 8, 2020.

* cited by examiner

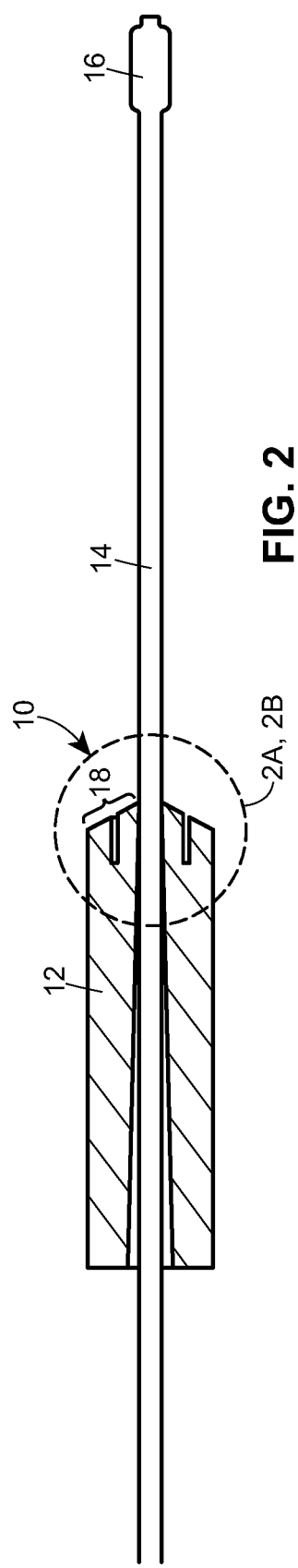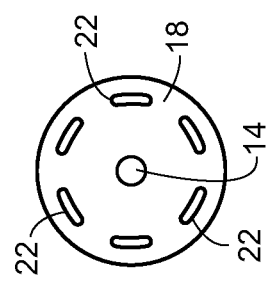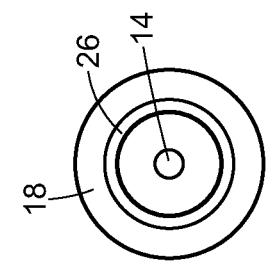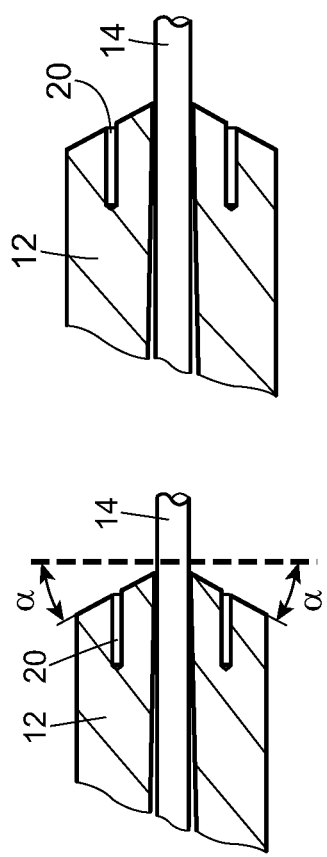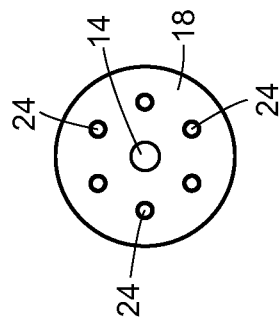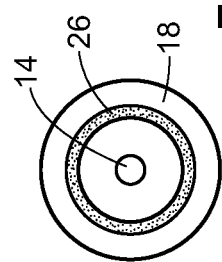

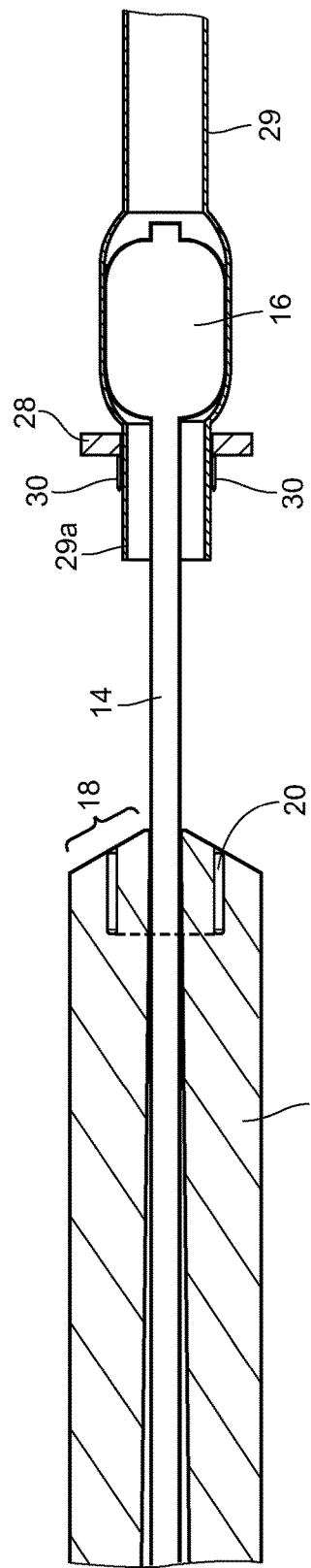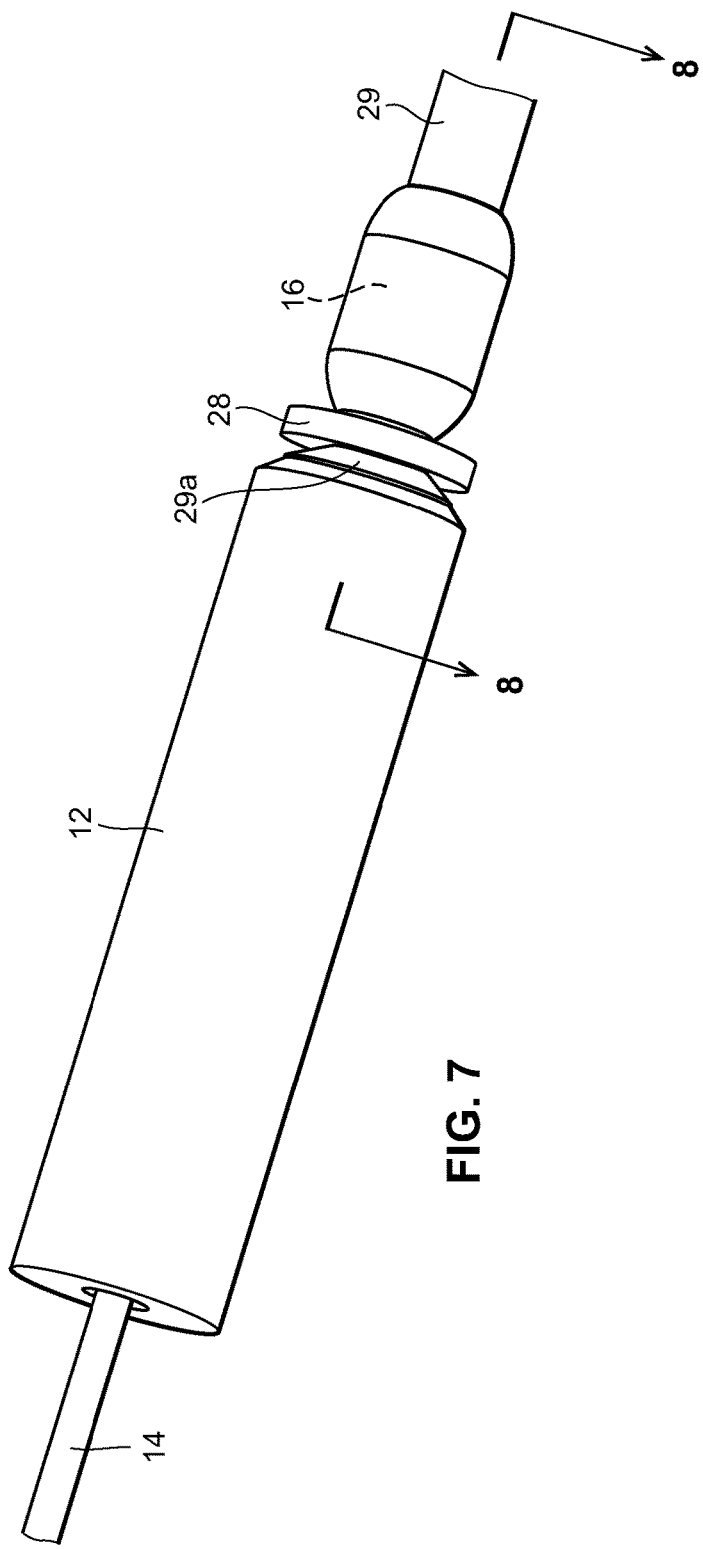

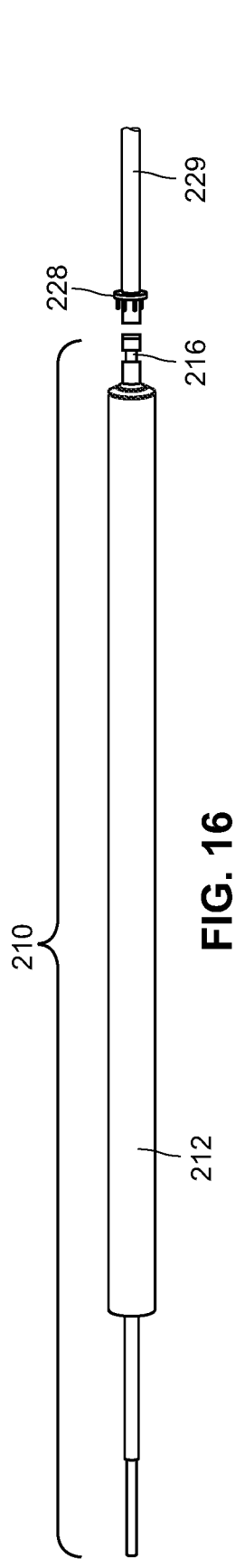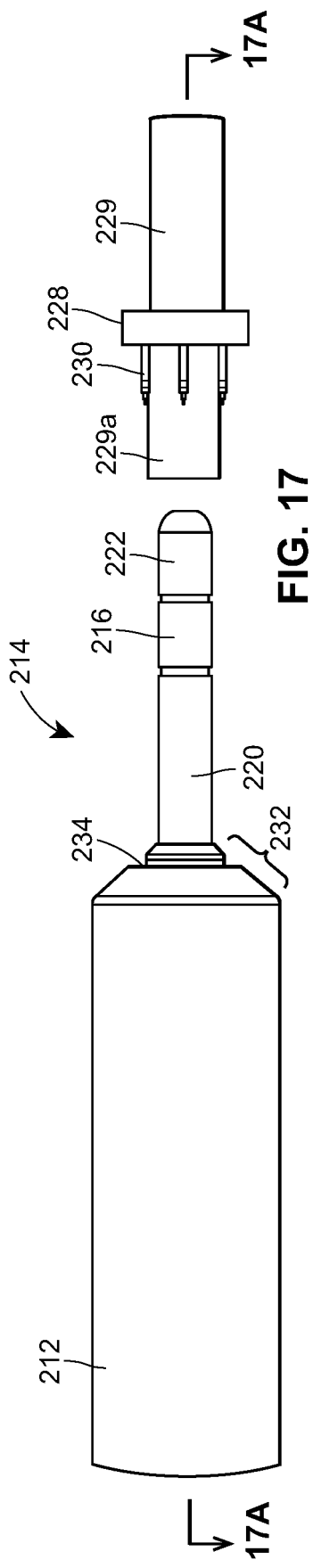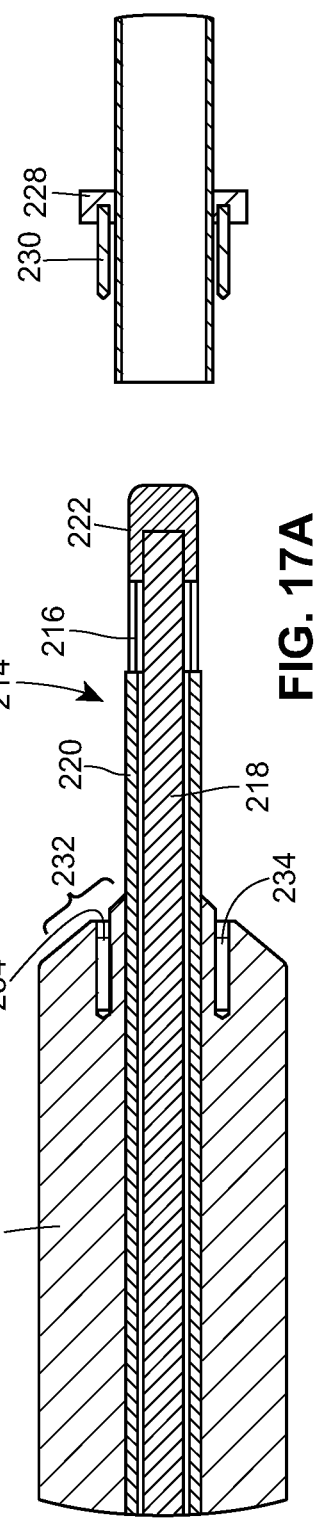

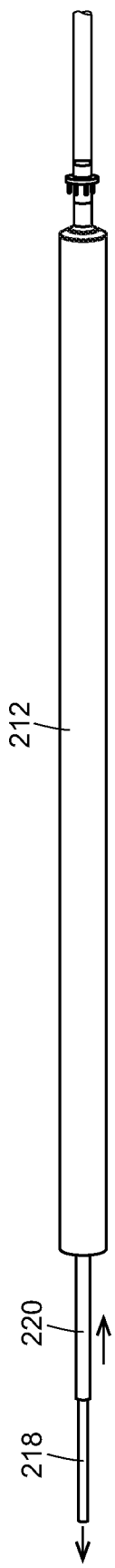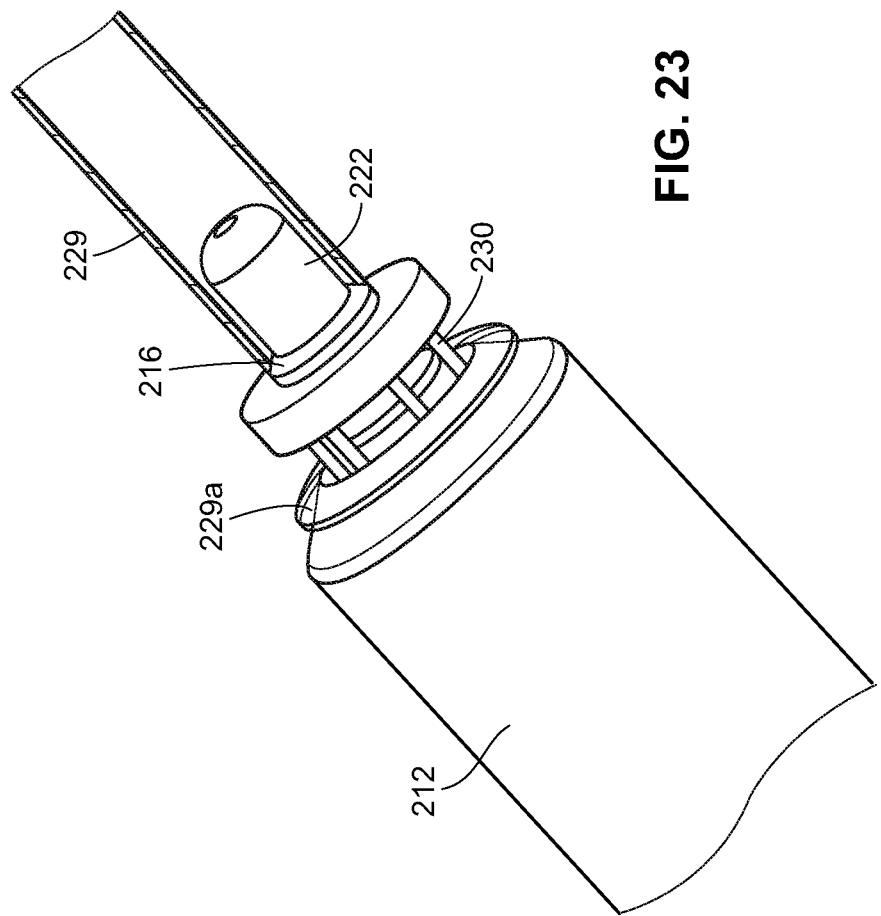

DEVICE TO AID IN ARTERIAL MICROVASCULAR ANASTOMOSIS

CROSS-REFERENCE TO RELATED APPLICATION

The present application is the US national phase of International Patent Application No. PCT/US2016/050037, filed Sep. 2, 2016, which claims the benefit of the filing date (under 35 USC 119(e)) of U.S. Provisional Application No. 62/214,615, filed Sep. 4, 2015. U.S. Provisional Application No. 62/214,615 is hereby incorporated by reference.

FIELD OF THE DISCLOSURE

This disclosure relates generally to microsurgical instruments and, more specifically, to devices that provide uniform or substantially uniform intraluminal support to an arterial segment in a manner that facilitates securing everted arterial tissue to a joinable ring or other coupler used in microvascular anastomosis.

BACKGROUND

Free tissue transfers from one part of a patient's body to another provide a means for reconstructive surgeons to repair and replace body parts, restoring appearance and in many cases function and feeling. The most common reasons for patients to undergo tissue transfers is after tumor extirpation (i.e. breast cancer reconstruction), trauma, burn injury, or to restore absent function associated with congenital anomalies.

In these tissue transfers, the microsurgeon removes tissue, including skin, fat, muscle, nerves and bone, with an associated vascular pedicle, from one part of the body and moves it to the part of the body where it is needed for aesthetic or functional restoration. The arteries and veins are re-attached and, in some cases, the nerves are as well. The surgical reattachment of veins and arteries is called microvascular anastomosis, occasionally referred to herein for the sake of brevity as microanastomosis. This procedure helps to restore blood circulation, and consequently, oxygen supply to the transferred tissue.

Microvascular anastomosis is the surgical coaptation of veins and arteries. Microvascular anastomosis of veins is readily accomplished using a microanastomotic coupling device, such as the GEM FLOW COUPLER®, which reduces complication rates, improves patency rates, substantially reduces the time necessary to complete the coaptation compared to manual suturing techniques, and can allow for blood flow monitoring so the vessel patency can be checked postoperatively.

However, microanastomosis of arteries is most often accomplished with standard manual suturing techniques because the thick, muscular wall of the arteries precludes use of the current microanastomotic couplers. The thick wall of the artery prevents the tissue of the arterial wall from being stretched over the rings of a coupler. Each microanastomotic coupler ring has a plurality of pins or posts, which are used to secure an everted portion of a vessel segment to the ring. Even after securing one portion of an everted arterial segment to a pin or post (or even a few pins or posts) of a microanastomotic coupler ring, efforts to secure remaining portions of the everted arterial segment to the coupler ring are often complicated by the first portion coming off the previously-secured pin(s) or post(s). Due to the lack of a reliable device or technique to avoid this problem, manual suturing is predominantly used for surgical coaptation of arteries.

Microscopic manual suturing of arteries can be quite challenging, primarily due to the small size of the vessels and the minimal working space. Since most vessels are only 1 to 3 mm in diameter, the procedure requires the use of a surgical microscope. The sutures are about 70 μm thick and can be difficult to handle. As a result, surgeons and surgical residents must undergo extensive additional training prior to operating on a patient in need of tissue transfer. Moreover, surgeons attempt to limit the recipient site morbidity resulting in small incisions and small areas within which to work. For instance, in microsurgical postmastectomy breast reconstruction, the surgeon will typically be working in a 2.5 to 3 cm surgical field. These size constraints make it difficult for surgeons to maneuver their surgical instruments. Arterial microanastomoses performed by manual suturing take approximately 23.5 minutes in the operating room, versus coaptation times as low as 5 minutes or less that would be possible if a surgeon were using a coupling device.

SUMMARY OF THE DISCLOSURE

Various embodiments of devices are disclosed herein that make arterial microanastomosis easier and more time-efficient by eliminating the need for sutures and enabling the use of the microanastomotic coupler. Simplifying the arterial microanastomotic procedure minimizes required exercise of operator skill, reduces the duration of intense concentration, and helps reduce the surgeon's fatigue during long, complex operative procedures. In each of the disclosed embodiments, a device provides a mechanism for delivering a uniform or substantially uniform intraluminal force behind or within a coupling ring of a microanastomotic coupler. In a first embodiment, the intraluminal force is supplied by an intraluminal catheter balloon inserted in an uninflated state into an arterial segment past a microanastomotic coupler ring through which the arterial segment extends. An everting tool, preferably having a conical end, is provided coaxially with a fluid conduit via which the catheter balloon can be inflated and deflated. In use, each of two arterial segments to be attached via microanastomosis is inserted through a respective microanastomotic coupler ring. Like in the case of venous microanastomosis, the coupler ring is positioned sufficiently proximal to the open (distal) end of the arterial segment to permit an exposed end portion of the arterial segment to be everted and secured to the pins or posts of the coupler ring.

The device of the present disclosure, with an uninflated intraluminal catheter balloon at the leading end thereof, is then aligned coaxially with one of the coupler rings and advanced toward the coupling ring until the catheter balloon is inserted into the arterial segment, past the coupler ring. Next, the intraluminal catheter balloon is inflated, such as by activating a syringe, piston, or plunger associated with the fluid conduit of the catheter balloon. When inflated, the catheter balloon provides a substantially uniform stabilizing force radially outward and in a direction toward a side of the coupler ring opposite the securement pins or posts. Next, the everting tool is advanced toward the coupling ring. The conical leading end of the everting tool is provided with slots or apertures, or a continuous annular channel, to receive the plurality of pins or posts of the coupler ring after they have pierced the everted arterial tissue. The slots, apertures, or continuous channel could be filled with a deformable, penetrable, or axially-receding member, such as a soft, rubber or rubber-like material, such that the pins or posts can easily push into, through, or past the deformable, penetrable, or axially-receding member. The slots, apertures, or channels could also, or alternatively, include a covering to promote sliding of the everter along the arterial tissue to help with everting the tissue over a coupler ring. Once the everted arterial tissue of the arterial segment to be coupled is adequately secured to the coupler ring, the intraluminal catheter balloon can be deflated and removed from the arterial segment. When both arterial segments are prepared for coaptation in this manner, the microanastomotic coupler can then be actuated to secure the coupler rings carrying the two arterial segments together.

In an alternate embodiment, instead of a catheter balloon, the device of the present disclosure is provided with an intraluminal shaft that can be telescopically extended into the arterial segment to provide the desirable supporting force.

In a further alternate embodiment, the device of the present disclosure features an intraluminal member that is inserted into an arterial segment, and the intraluminal member includes an expandable mechanism by which at least a portion of the intraluminal member radially expands at a location coincident with, or at least overlapping with, an interior of the coupler ring. Radial forces exerted by this intraluminal mechanism on the wall of the arterial segment provides sufficient support to facilitate eversion of an exposed region of the arterial segment and securement of that everted region to the posts or pins of the coupler ring.

In yet a further embodiment, at least a portion of, and preferably at least a majority of, and optionally, an entire, eversion surface of the device of the present disclosure is made of a pierceable material, which permits the pins of the coupler to penetrate the eversion surface and project into the device without significant deformation of the coupler pins. By way of example, the eversion surface may be manufactured of a medical grade silicone having a Shore A hardness between 10 and 50. The pierceable material may extend beyond the eversion surface, the majority of the length of, substantially the entire length of, or the entire length of, the eversion device. A supporting rod can be included within, outside, or a combination of within and outside the tool so as to maintain the structural rigidity of the tool. By way of example, the supporting rod may be a stainless steel rod embedded within the tool.

The supporting rod may be sufficiently ductile such that it is deformable by the user, enabling the user to customize the shape of the tool so as to manipulate it for maneuverability in small and hard to reach areas. Furthermore, the device of the present disclosure may be provided with an eversion surface at either end of the device, allowing for a greater size range of vessels and couplers to be accommodated with a single eversion tool.

BRIEF DESCRIPTION OF THE SEVERAL VIEWS OF THE DRAWINGS

FIG. 2 is a longitudinal cross-sectional view, taken along lines 2-2 of FIG. 1; of the arterial everter device illustrated in FIG. 1;

FIG. 2A is an enlarged region of the longitudinal cross-sectional view of FIG. 2 denoted by the dashed line 2A in FIG. 2;

FIG. 2B is an enlarged region of the longitudinal cross-sectional view of FIG. 2 denoted by the dashed line 2B in FIG. 2;

FIG. 2C is an end view of the everter end of the arterial everter illustrated in FIG. 2B, provided with a circumferential slot to receive the pins or posts of a coupler ring;

FIG. 2D is an end view of an alternate everter end of the arterial everter illustrated in FIG. 2B, provided with a set of arcuate slots to receive the pins or posts of a coupler ring;

FIG. 2E is an end view of another alternate everter end of the arterial everter illustrated in FIG. 2B, provided with a region made of a deformable or piercable material so as to receive the pins or posts of a coupler ring;

FIG. 2F is an end view of yet another alternate everter end of the arterial everter illustrated in FIG. 2B, provided with a set of circular openings to receive the pins or posts of a coupler ring;

FIG. 6 is an enlarged longitudinal cross-sectional view, taken along lines 6-6 of FIG. 5, of the arterial everter device and arterial segment with coupler ring of FIG. 5;

FIG. 7 is an enlarged perspective view of the arterial everter device of the first embodiment with an everting member thereof advanced toward the coupler ring and inflated intraluminal catheter balloon, the everting member, upon engagement with an exposed end region of the arterial segment and further advancement toward the coupler ring, everting the exposed region of the arterial segment and impaling that exposed region on the pins or posts provided on a first, coupling side of the coupler ring;

FIG. 16 is a perspective view of an arterial everter device of a third embodiment of the present disclosure, the arterial everter device including a telescopically-mounted intraluminal probe having a radially expanding member thereon, approaching a first arterial segment having a coupler ring disposed near an open and thereof;

FIG. 17 is an enlarged plan view of the arterial everter device of the third embodiment approaching a first arterial segment having a coupler ring disposed near an open end thereof;

FIG. 17A is a cross-sectional view taken along lines 17A-17A of FIG. 17;

FIG. 22 is a perspective view of the arterial everter device of the third embodiment, the arterial segment, and the coupler ring, with directional arrows indicating movement of an inner shaft relative to an outer shaft to expand the radially expanding member;

FIG. 23 is an enlarged perspective view of the arterial everter device of the third embodiment, with an everting member thereof advanced toward the coupler ring, the telescopically-mounted intraluminal probe including an expander outer shaft, an expander inner shaft, and end cap, with the radially expanding member being in the form of an expansion ring disposed between a proximal end of the end cap and a distal end of the expander outer shaft, linear movement of the expander inner shaft and proximal end of the end cap toward the distal end of the expander outer shaft reducing an axial distance between the proximal end of the end cap and the distal end of the expander outer shaft thereby causing radial expansion of the expansion ring, further advancement of the everting member toward the coupler ring and along the expander shaft effectively retracting a region of the telescopically-mounted intraluminal probe into the everting member, and the everting member, upon engagement with an exposed end region of the arterial segment and further advancement toward the coupler ring, everting the exposed region of the arterial segment and impaling that exposed region on the pins or posts provided on a first, coupling side of the coupler ring;

DETAILED DESCRIPTION OF THE PREFERRED EMBODIMENTS

Figure 1:
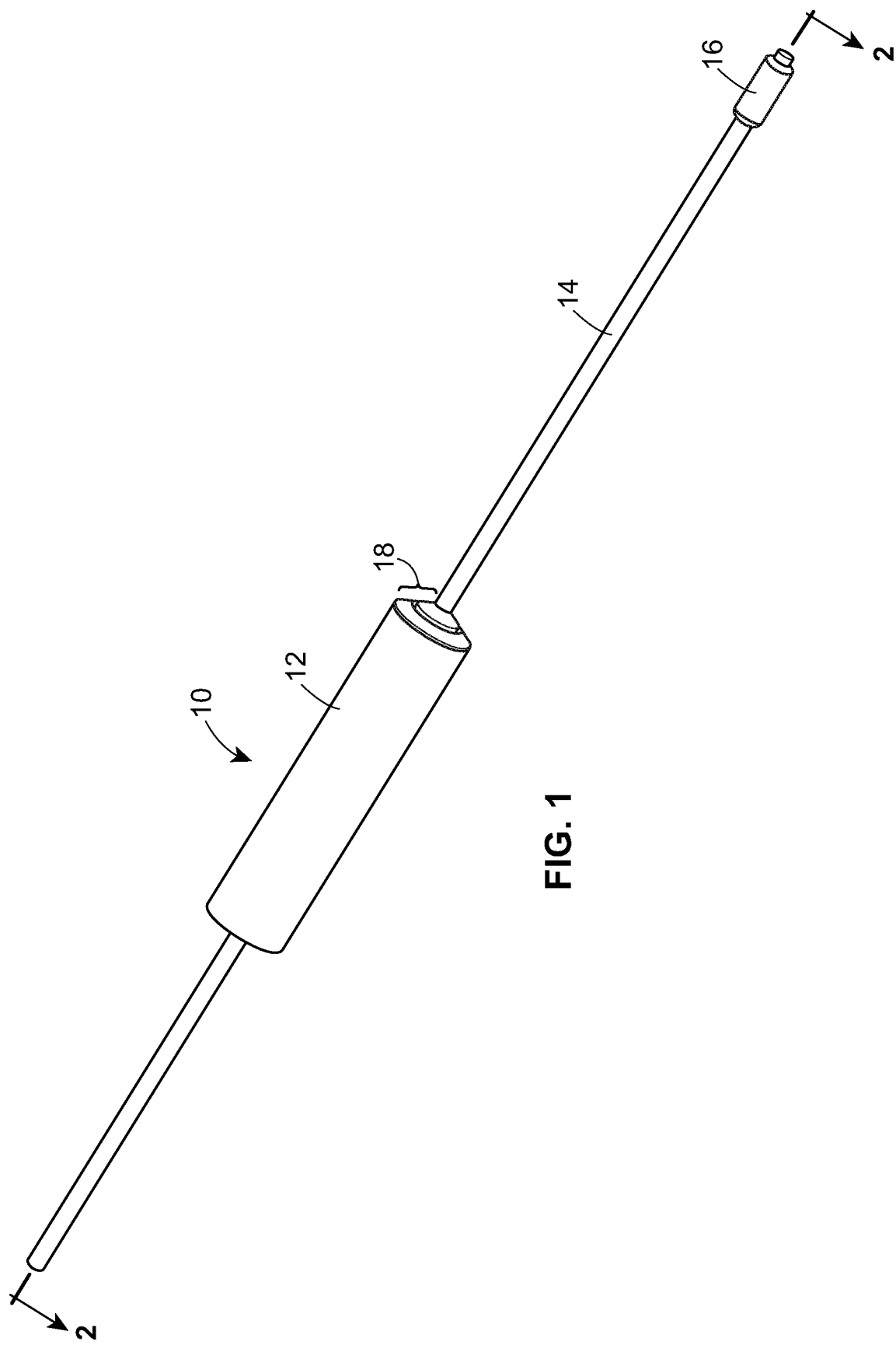
FIG. 1 is a perspective view of an arterial everter device of a first embodiment of the present disclosure.

In an effort to promote efficiency in the execution of an arterial microanastomosis procedure, it is found that the challenges presented by the relatively thick wall of an artery (as compared to the wall thickness of a vein) can be mitigated by applying uniform support to a region of an arterial segment just behind, and/or within, a coupler ring of an anastomosis clamp system such as the such as the GEM FLOW COUPLER® of Synovis Micro Companies Alliance, Inc., a division of Baxter. Uniform eversion of the arterial segment over the coupler pins, instead of asymmetrically everting a portion of the arterial segment over just one or a few pins or posts of the coupler ring at a time, also helps mitigate challenges posed by relatively thick walls of arteries.

As illustrated in FIGS. 1-8, an arterial everter device 10 of a first embodiment of the present disclosure includes an everting member 12, a hollow inflation shaft 14, and an intraluminal catheter balloon 16 disposed at a distal end of the hollow inflation shaft 14. The intraluminal catheter balloon 16 has a nominal deflated diameter less than a nominal inner diameter of an arterial segment 29 for which the arterial everter device 12 is to be used. The intraluminal catheter balloon 16 preferably has a nominal inflated diameter that is at least just greater than the nominal inner diameter of the arterial segment 29, so as to put pressure on the arterial wall when inflated, thereby providing a holding force. The intraluminal catheter balloon 16 may or may not accommodate over-inflation, i.e. inflation beyond a nominal inflated diameter that is just greater than the nominal inner diameter of the arterial segment 29. For instance, arteries typically involved in microvascular anastomosis generally have a diameter ranging from 1 mm to 4 mm. An intraluminal catheter balloon 16 for use with arterial segments having a 1 mm diameter preferably has a nominal deflated diameter in a range of 0.5-0.9 mm and an inflated diameter of 1.5-2.5 mm. An intraluminal catheter balloon 16 for use with arterial segments having a 3 mm diameter preferably has a nominal deflated diameter in a range of 1.4-2.9 mm and an inflated diameter of 3.5-4.5 mm.

The everting member 12 is longitudinally slidable along an exterior of the hollow inflation shaft 14. An everter end 18 of the everting member 12 is preferably conical in shape and may have an angle α (see FIG. 2A) between 10° and 60°. This angle of the everter end 18 may be a constant angle or, alternatively, may be a progressively changing angle.

The everting member 12 is provided with one or more pin- or post-receiving openings 20, which may be in the form of a continuous circumferential (i.e., annular) slot (as illustrated in FIG. 2C), or discontinuous openings 20, such as in the form of interrupted arcuate openings 22 or round openings 24 (as illustrated in FIGS. 2D, 2F, respectively) that accommodate pins or posts 30 of a coupler ring 28. Alternatively, at least a portion 26 of the everter end 18 is formed of a compliant material that deforms, such as a thermoplastic elastomer or silicone rubber (as depicted by the stippled region in FIG. 2E) to receive the pins or posts 30 of the coupler ring 28, or a material that can be pierced (as also depicted by the stippled region in FIG. 2F) by the pins or posts 30 of the coupler ring 28. Alternately, the portion 26 of the everter end 18 may be a slideable member that axially recedes into the everter to receive the pins or posts after they move through the arterial segment.

Figure 3:
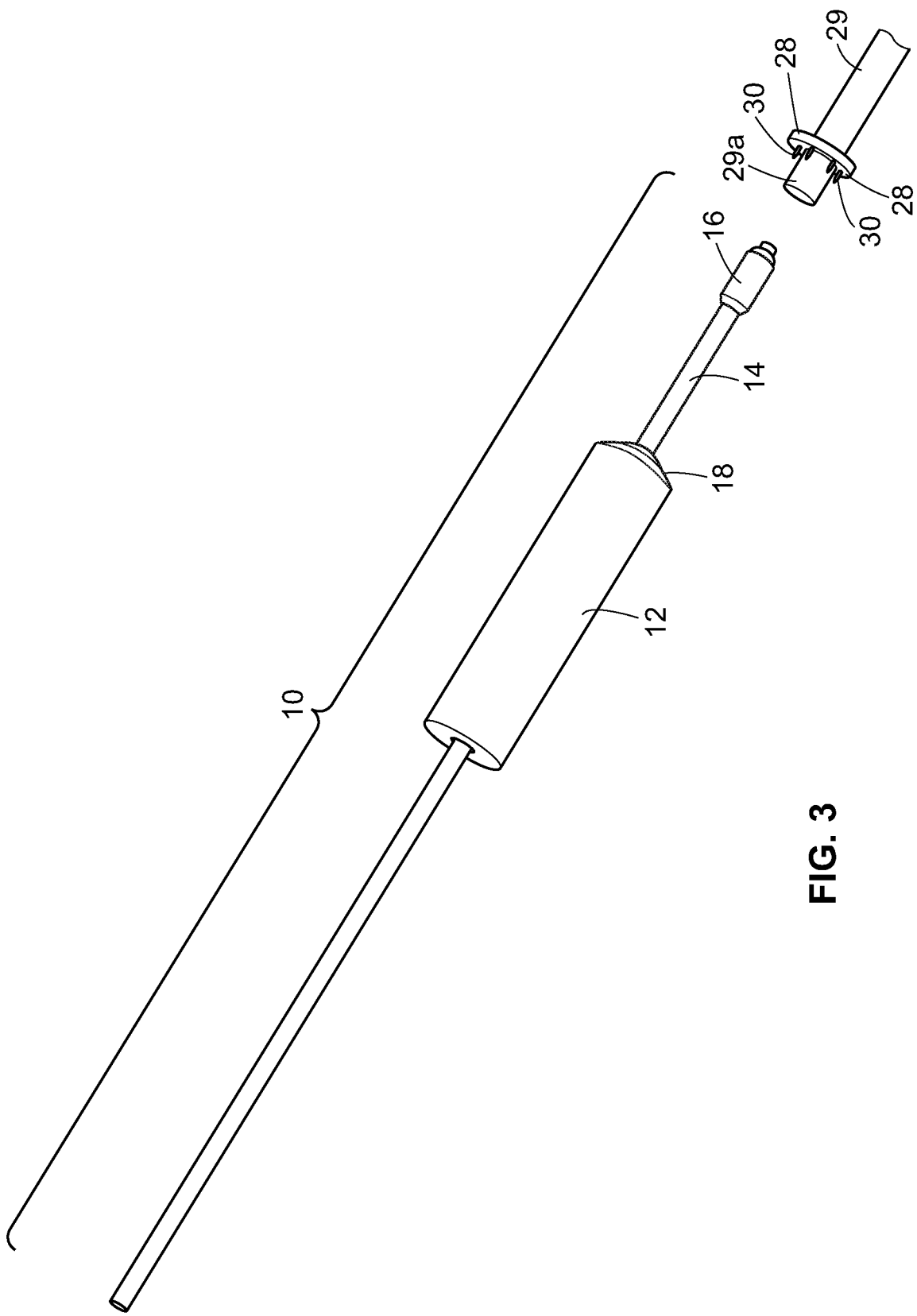
FIG. 3 is a perspective view of the arterial everter device illustrated in FIG. 1, with an intraluminal catheter balloon in a deflated condition, approaching a first arterial segment having a coupler ring disposed near an open end thereof.
Figure 4:
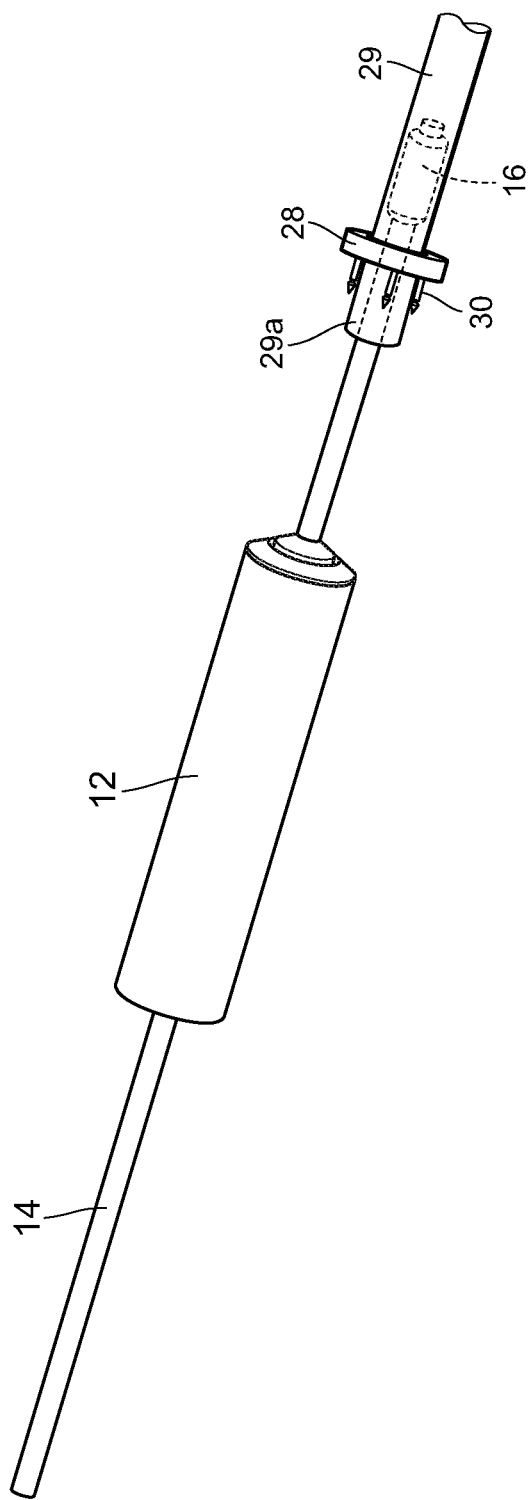
FIG. 4 is a perspective view similar to that of FIG. 3, but illustrating the arterial everter device of the first embodiment advanced toward and into the arterial segment, such that an entirety of the intraluminal catheter balloon (illustrated in hidden lines), still in its deflated condition, is disposed beyond the coupler ring.

The coupler ring 28 is provided near a free end region 29a of an arterial segment 29 that is to be surgically coapted to another arterial segment (not shown) using microanastomosis. The coupler ring 28 is arranged with its pins or posts 30 directed toward the free end region 29a. The arterial segment 29 is part of an artery that has been clamped by a vessel clamp (not shown) upstream of the coupler ring 28 and has been irrigated. As illustrated in FIGS. 3, 4, the arterial everter device 10 is advanced toward the arterial segment 29 until the intraluminal catheter balloon 16, while in an uninflated condition, is received in the arterial segment 29 and is disposed just beyond the coupler ring 28.

Figure 5:
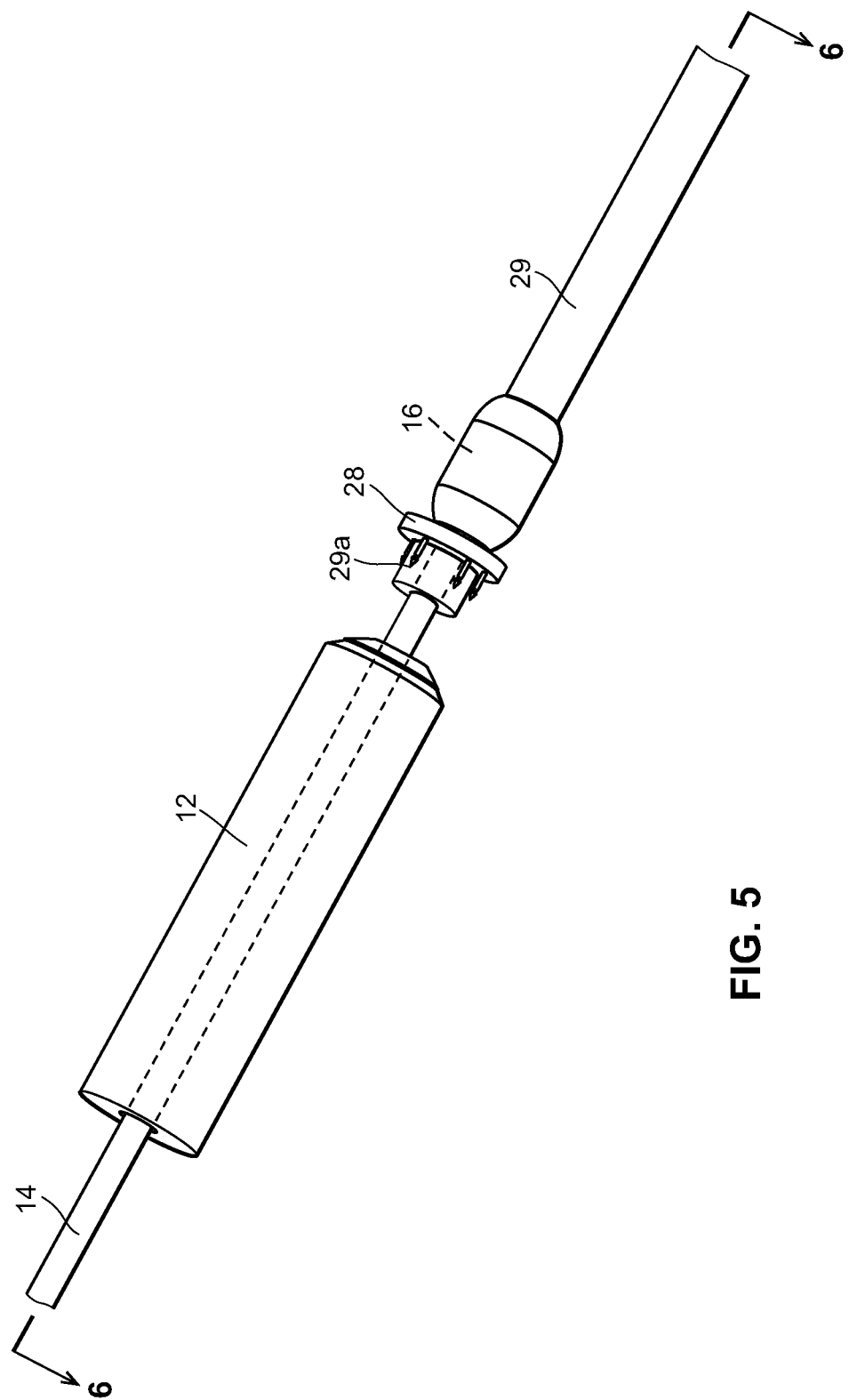
FIG. 5 is a perspective view similar to that of FIG. 4, but illustrating the intraluminal catheter balloon of the arterial everter device in an inflated condition.

Next, using a syringe or other fluid media introducing device (not shown) provided, for example, at a proximal end of the arterial everter device 10 in fluid communication with the hollow inflation shaft 14, the intraluminal catheter balloon 16 is inflated (see FIGS. 5, 6). Once the intraluminal catheter balloon 16 is inflated to at least its nominal inflated diameter, the intraluminal balloon 16 applies even, radially outward pressure on the artery, which serves the following advantages: First, the intraluminal balloon 16 provides an atraumatic hard-stop for the coupler 28 so as to maintain the proper length of the free end region 29a of the arterial segment 29 to be everted over the pins or posts of the coupler ring 28; Second, the intraluminal balloon 16 opposes the axial forces placed on the free end region 29a as the everting member 12 is advanced toward the free end region 29a; and Third, the intraluminal balloon 16 minimizes the unsupported length of the free end region 29a, thereby reducing the tendency for buckling.

Figure 8:
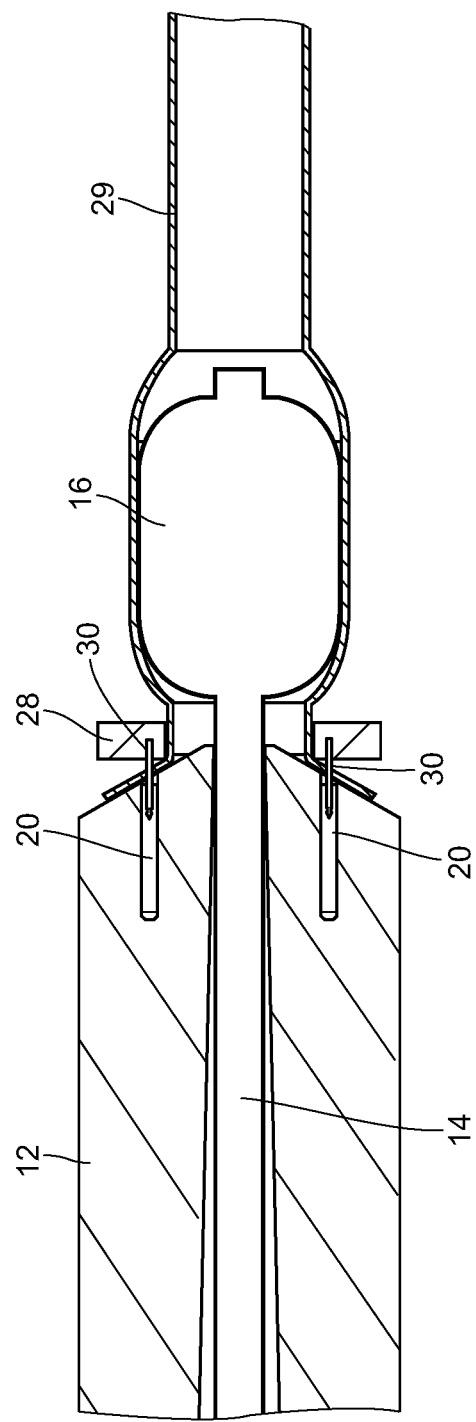
FIG. 8 is an enlarged longitudinal cross-sectional view, taken along lines 8-8 of FIG. 7.
Figure 9A:
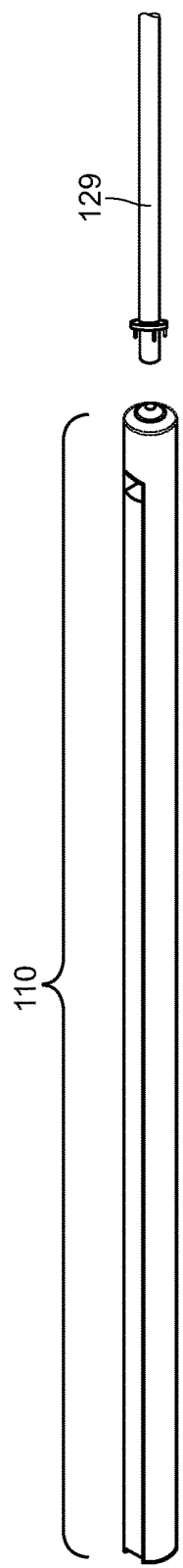
FIG. 9A is a perspective view of an arterial everter device of a second embodiment of the present disclosure, approaching a first arterial segment having a coupler ring disposed near an open end thereof.
Figure 9B:
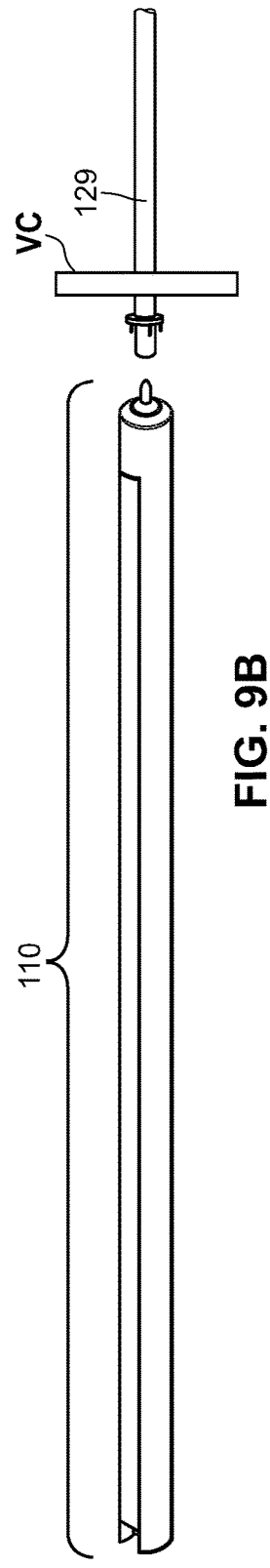
FIG. 9B is a perspective view similar to FIG. 9A, but illustrating (schematically) a vessel clamp secured to the first arterial segment upstream of the coupler ring (i.e., on a side of the coupler ring opposite the free end of the arterial segment), and illustrating a retractable telescopically-mounted plunger of the arterial everter device advanced distally of an everter end.
Figure 10:
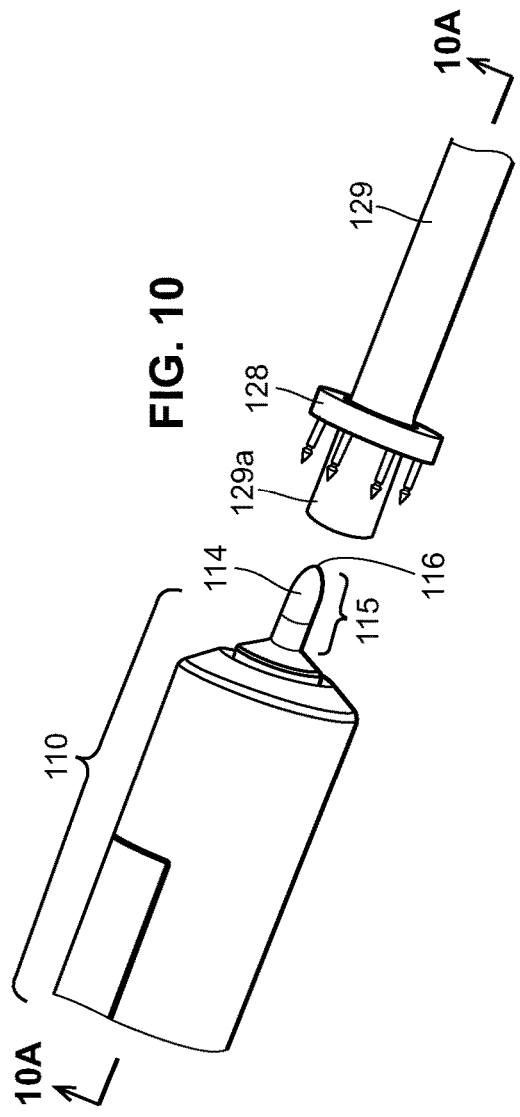
FIG. 10 is an enlarged perspective view of the arterial everter device of the second embodiment approaching a first arterial segment having a coupler ring disposed near an open end thereof.
Figure 10A:
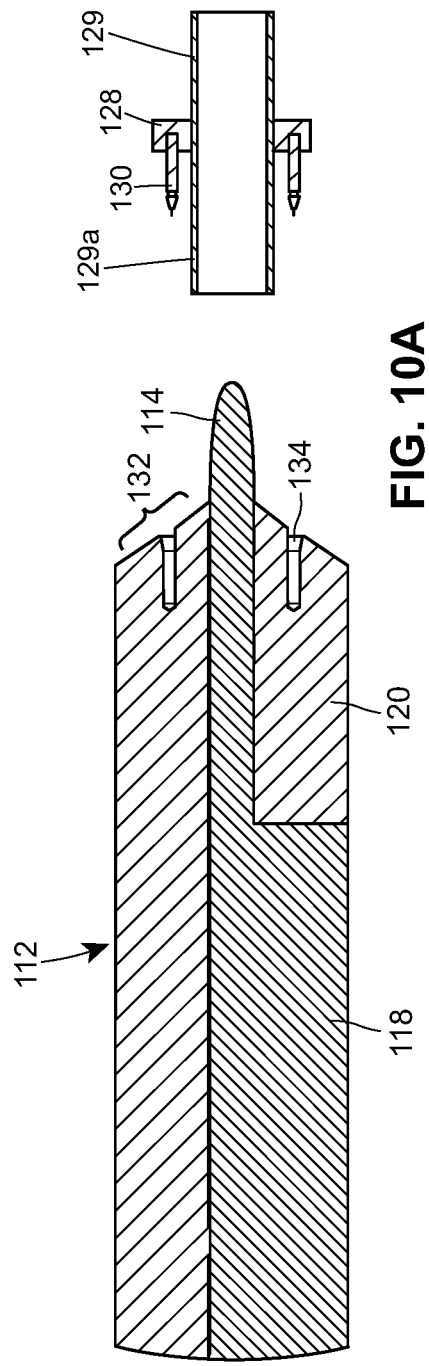
FIG. 10A is a cross-sectional view of the arterial everter device, first arterial segment, and coupler ring illustrated in FIG. 10.
Figure 10B:
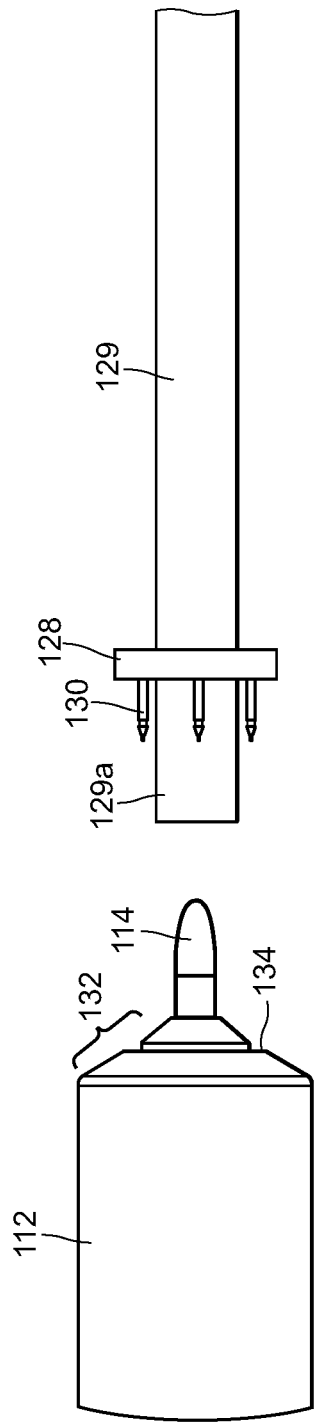
FIG. 10B is a plan view of the arterial everter device, first arterial segment, and coupler ring illustrated in FIG. 10.
Figure 11:
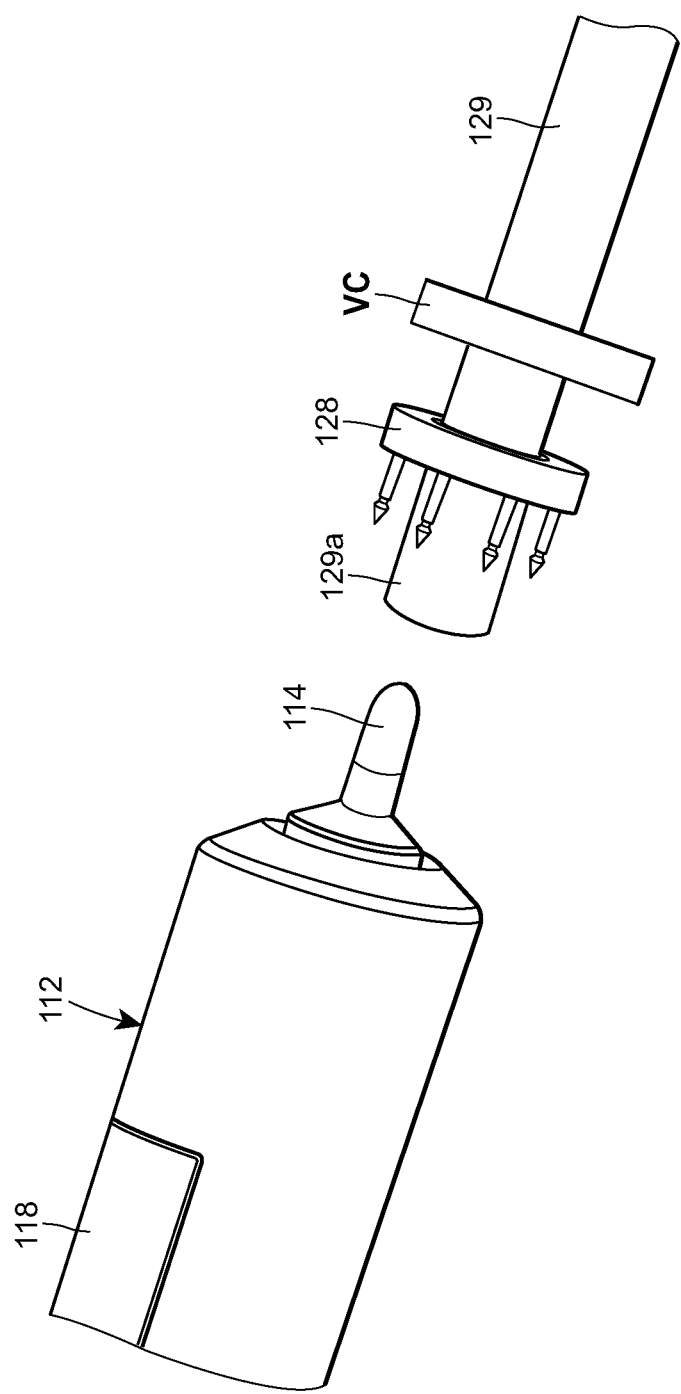
FIG. 11 is an enlarged perspective view similar to FIG. 10, further illustrating a vessel clamp grasping the arterial segment on a side of the coupler ring opposite the free end of the arterial segment.
Figure 12:
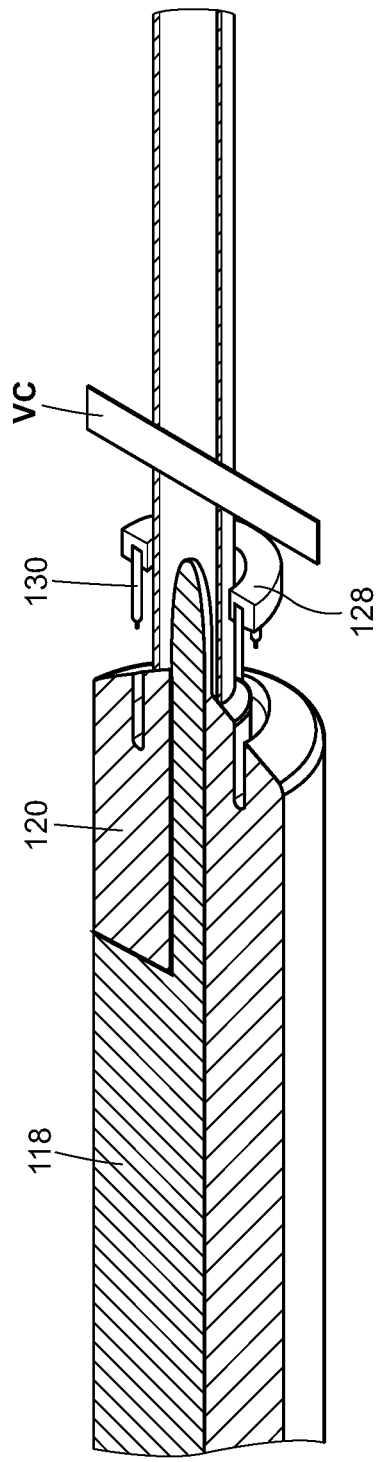
FIG. 12 is an enlarged longitudinal cross-sectional and orthogonal view illustrating the arterial everter device of the second embodiment advanced toward the arterial segment, with a telescopically-mounted plunger of the arterial everter device advancing into the arterial segment toward the location at which the arterial segment is grasped by the vessel clamp.
Figure 13:
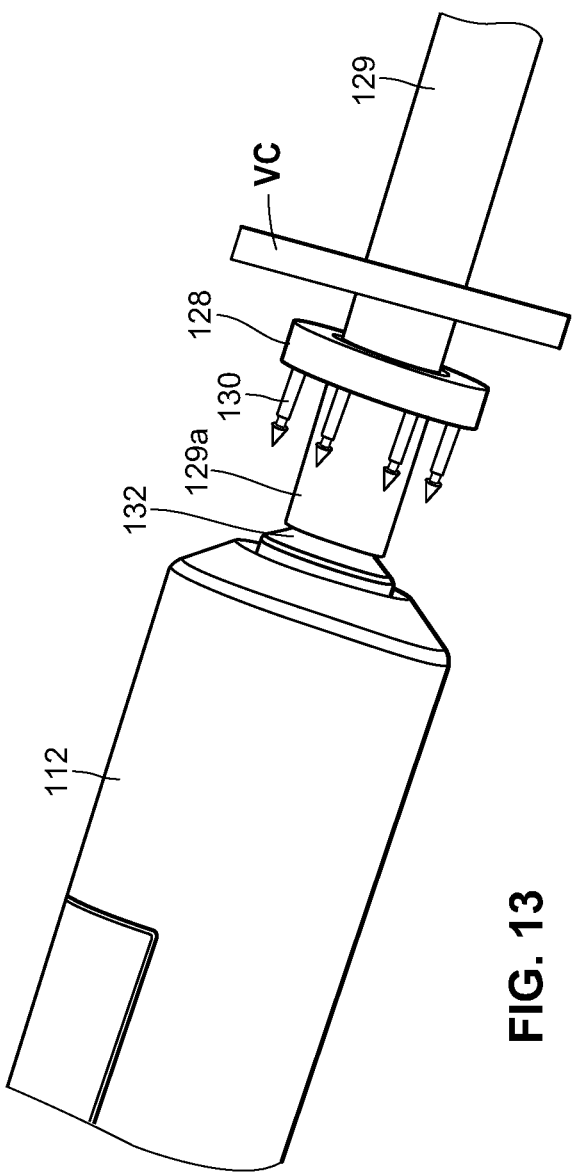
FIG. 13 is an enlarged perspective view illustrating the arterial everter device of the second embodiment in the condition illustrated in FIG. 12.

In an effort to simultaneously impale all of the pins or posts 30 of the coupler ring 28 through the free end region 29a of the arterial segment 29, the everting member 12 is advanced along the hollow inflation shaft 14 until the everter end 18 contacts the free end region 29a, with continued advancement of the everting member 12 toward the coupler ring 28 everting the free end region 29a of the arterial segment 29, as illustrated in FIG. 7. Sufficient force is applied to the everting member 12 in the direction of the coupler ring 28 to cause the pins or posts 30 of the coupler ring 28 to pierce through the arterial wall tissue of the free end region 29a of the arterial segment 29, and the pins or posts 30 are received in the pin- or post-receiving opening(s) 20, such as a circumferential slot, provided in the everter end 18, as illustrated in FIG. 8. With the free end region 29a of the arterial segment 29 secured to the coupler ring 28, the intraluminal catheter balloon 16 is then deflated and removed from the arterial segment 29.

The above procedure is repeated on another arterial segment (not shown) to be coapted to the first arterial segment 29, so as to secure a free end region of that other arterial segment to a mating coupler ring (also not shown), after which the two coupler rings can be brought together to complete the end-to-end microanastomosis.

Turning to FIGS. 9-15, a second embodiment of an arterial everter device 110 of the present disclosure and method for use of the arterial everter device for preparing an arterial segment 129 for an end-to-end microanastomosis are illustrated. The arterial everter device 110 includes an everting member 112 and a telescopically-mounted plunger 114. The telescopically-mounted plunger 114 may be made of a rigid material, such as a thermoplastic or stainless steel, a flexible material, such as a thermoplastic elastomer or silicone rubber, or a composite of rigid and flexible materials. A distal portion 115 of the telescopically-mounted plunger 114 may terminate in a bullet-shaped end 116. At least the distal portion 115 of the telescopically-mounted plunger 114 preferably has an outer diameter less than or equal to an inner diameter of the arterial segment 129 into which it is intended to be inserted. As in the case of the previous embodiment, the arterial segment 129 is prepped for end-to-end microanastomosis by providing a coupler ring 128 near a free end 129a of the arterial segment 129, with a plurality of pins or posts 130 of the coupler ring 128 directed toward the free end 129a, and the arterial segment 129 received in the inner opening of the coupler ring 128. A vessel clamp VC, such as a microvascular clamp, is clamped to the arterial segment 129 upstream of the coupler ring 128, the vessel clamp VC preventing the arterial segment 129 from sliding back through the coupler ring 128. The free end 129a is irrigated.

The arterial everter device 110, with the telescopically-mounted plunger 114 in its fully extended position, is advanced toward, and into, the free end region 129a of the arterial segment 129 until the distal end 116 of the plunger 114 contacts an inner wall of the arterial segment at the location of the vessel clamp VC (i.e., the plunger 114 is brought into contact with arterial tissue that is abutting the vessel claim VC). The arterial everter device 110 is further advanced toward the free end region 129a and the coupler ring 128, due to interference with the vessel clamp VC, the plunger 114 ceases to advance along the interior of the arterial segment 129. Instead, a main body 118 of the plunger 114, which is housed within and axially slidable relative to a housing 120 of the everting member 112, effectively retracts some length of the plunger 114 into the housing 120.

As in the case of the first embodiment described above, the everting member 112 includes an angled everter end 132.

The angled everter end 132 includes one or more post- or pin-receiving openings 134, such as a continuous circumferential (i.e., annular) slot.

Figure 14:
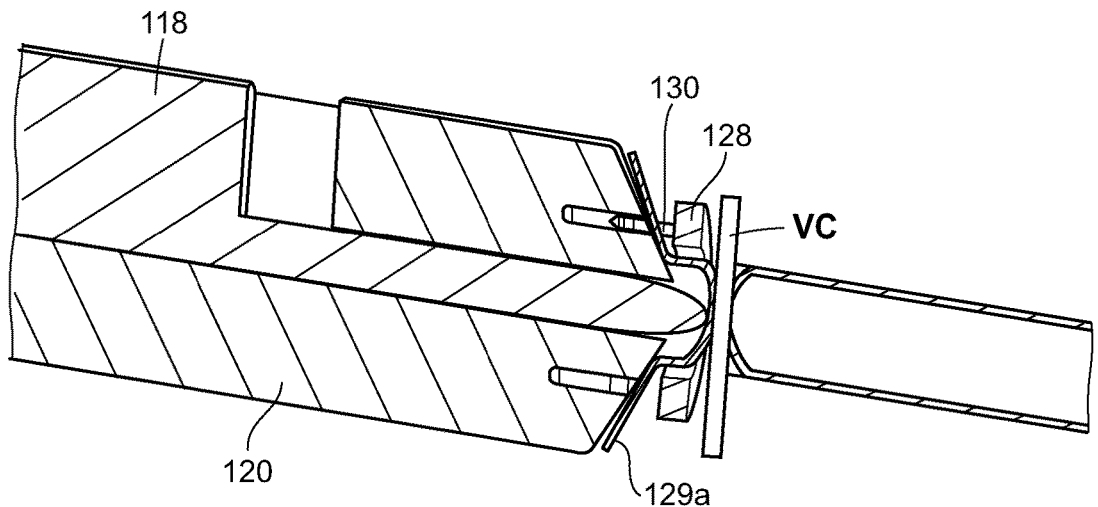
FIG. 14 is an enlarged cross-sectional view of the arterial everter device of the second embodiment with an everting member thereof advanced toward the coupler ring, the telescopically-mounted plunger ceasing advancement upon contact with the interior wall of the portion of the arterial segment grasped by the vessel clamp and further advancement of the everting member toward the coupler ring so as to effectively retract a region of the plunger into the everting member, and the everting member, upon engagement with an exposed end region of the arterial segment and further advancement toward the coupler ring, everting the exposed region of the arterial segment and impaling that exposed region on the pins or posts provided on a first, coupling side of the coupler ring.
Figure 15:
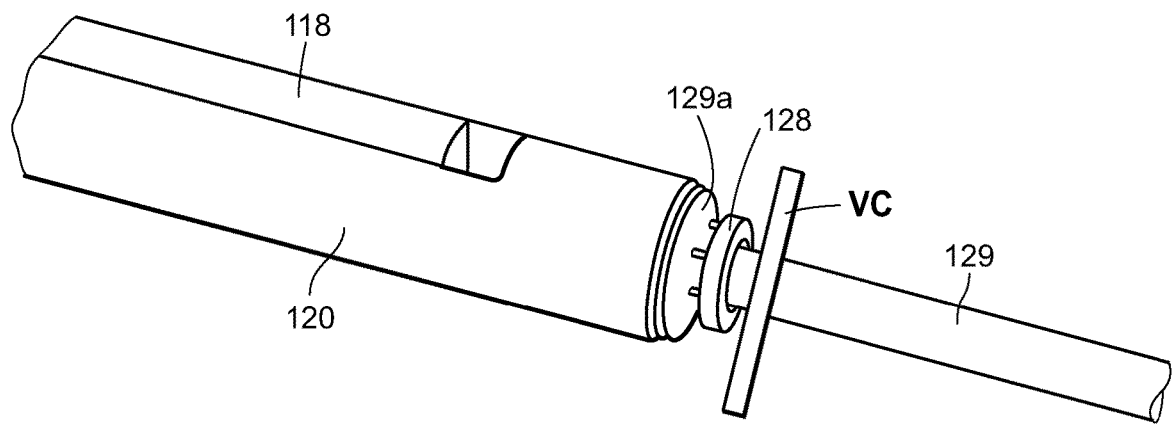
FIG. 15 is an enlarged perspective view illustrating the arterial everter device of the second embodiment and the arterial segment, coupler ring, and vessel clamp in the condition illustrated in FIG. 14.
Figure 18:
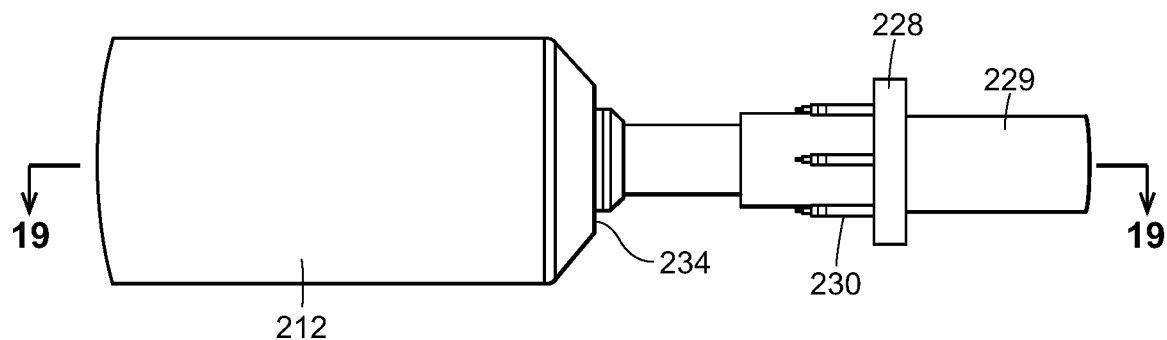
FIG. 18 is an enlarged plan view of the arterial everter device of the third embodiment, the intraluminal probe advanced into the arterial segment with the radially expanding member of the intraluminal probe in a collapsed condition, the radially expanding member positioned in the arterial segment so as to be aligned with an interior of the coupler ring.
Figure 19:
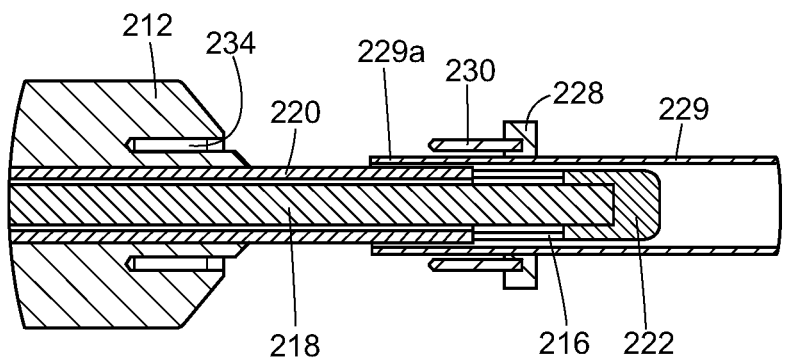
FIG. 19 is a longitudinal cross-sectional view, taken along lines 19-19 of FIG. 18, of the arterial everter device of the third embodiment, with the radially expanding member of the intraluminal probe still in the collapsed condition.
Figure 20:
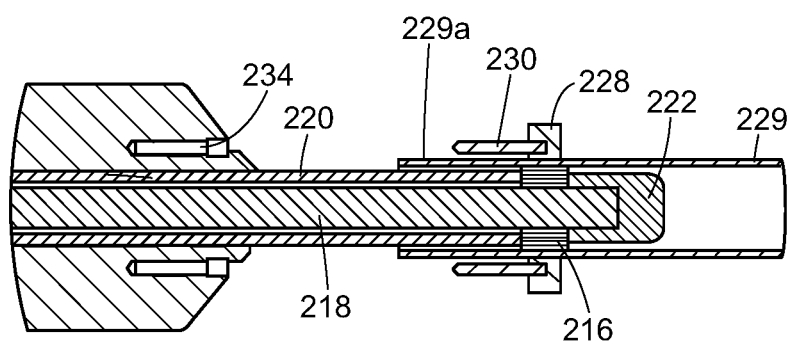
FIG. 20 is a longitudinal cross-sectional view of the arterial everter device of the third embodiment similar to FIG. 19, but illustrating the radially expanding member in a radially expanded condition.
Figure 21:
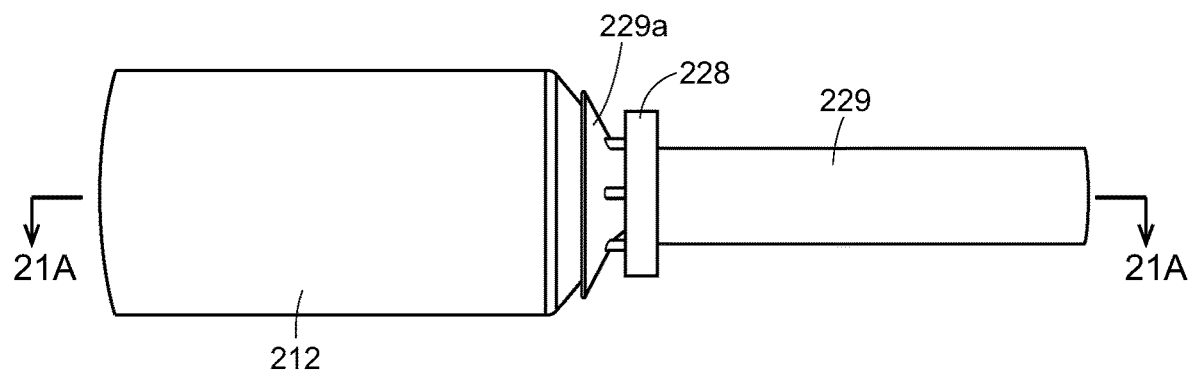
FIG. 21 is an enlarged perspective view of the arterial everter device of the third embodiment, the arterial segment, and the coupler ring, with the radially expanding member in the radially expanded condition.
Figure 21A:
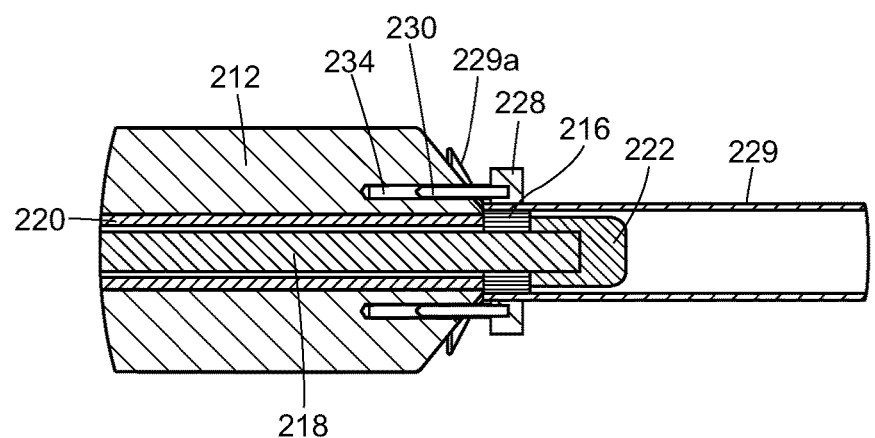
FIG. 21A is a cross-sectional view taken along lines 21A-21A of FIG. 21.

When the everting member 112 is sufficiently advanced toward the free end region 129a of the arterial segment 129 so as to contact the arterial tissue, the everter end 132 is further advanced toward the coupler ring 128, with the angled everter end 132 everting the free end region 129a of the arterial segment 129, as illustrated in FIGS. 14, 15. The still-exposed (relative to the angled everter end 132 of the everting member 112) portion of the plunger 114 serves to maintain the shape of the arterial vessel and prevent the free end region 129a of the arterial segment 129 from bucking inward so as to permit a substantially continuous application of force annually along the coupler ring 128 to offset the tendency of the relatively thick arterial tissue to recover its natural shape and lose engagement with the pins or posts 130 of the coupler ring 128 as the arterial tissue is everted and secured to the coupler ring 128. Sufficient force is applied to the everting member 112 in the direction of the coupler ring 128 to cause the pins or posts 130 of the coupler ring 128 to pierce through the arterial wall tissue of the free end region 129a of the arterial segment 129, and the pins or posts 130 are received in the pin- or post-receiving opening(s) 134, such as a circumferential slot, provided in the everter end 132, as illustrated in FIG. 14. The everting member 112 can then be withdrawn from the arterial segment 129. The process is repeated for another arterial segment (not shown) to be coapted to the first arterial segment 129, so as to secure a free end region of that other arterial segment to a mating coupler ring (also not shown), after which the two coupler rings can be brought together to complete the end-to-end microanastomosis.

A third embodiment of an arterial everter device 210 of the present disclosure is illustrated in FIGS. 16-23. The device includes an everting member 212, a shaft 214 that projects distally from an everter end 232 of the everting member 212, and a radially expanding member, such as an expansion ring 216, provided along the shaft 214. The shaft 214 preferably includes an inner shaft 218 that is axially movable relative to an outer shaft 220, the outer shaft 220 disposed in (preferably coaxially with) the everting member 212. The inner shaft 218 projects distally of a distal end of the outer shaft 220. The shaft 214 is additionally provided with an end cap 222 disposed at, and fixed to, a distal end of the inner shaft 218. The expansion ring 216, or similar radially expanding member, is disposed between a distal end of the outer shaft 220 and a proximal end of the end cap 222. The expansion ring 216, or similar radially expanding member, may be made of a flexible material, such as a thermoplastic elastomer or silicone rubber. The expanding member may alternately or additionally include a rigid material, such as a thermoplastic or stainless steel.

When the inner shaft 218 is pulled proximately relative to the outer shaft 220 of the shaft 214, the proximal end of the end cap 222 is pulled closer to the distal end of the outer shaft 220. This closer proximity of the end cap 222 to the distal end of the outer shaft 220 affords less axial room for the expansion ring 216 along the length of the shaft 214. As a result, the expansion ring 216 is compressed, whereupon it expands radially outwardly.

An arterial segment 229 is prepared for microanastomosis by applying a coupler ring 228 over a free end region 229a, with the arterial vessel received in an inner opening of the coupler ring 228. The coupler ring 228 is provided with a plurality of posts or pins 230 that project toward the distal end of the free end region 229a. The everter end 232 of the everting member 212 is provided with an angled everter end 232 that includes one or more post- or pin-receiving openings 234, such as a continuous circumferential (i.e., annular) slot.

In use, the arterial everter device 210 is advanced toward the free end region 229a until an exposed (relative the everter end 232) portion of the shaft 214, including the end cap 222 and the expansion ring 216 are inserted into the free end region 229a, with the expansion ring 216 positioned within the inner opening of the coupler ring 228. Next, the inner shaft 218 is pulled proximally so as to bring the end cap 222 closer to the distal end of the outer shaft 220, thereby causing the expansion ring 216 to expand radially outwardly, compressing the arterial vessel between the expansion ring 216 and an inner surface of the coupler ring 228. This expansion atraumatically holds the arterial vessel rigidly in place in relation to the coupler ring 228, while providing a supporting function that reduces the tendency of the free end region 229a to collapse, or buckle, during eversion.

With the arterial vessel rigidly secured in place, the everting member 212 is advanced toward the coupler ring 228, causing the free end region 229a to flare out over the post-or pin-receiving opening(s) 234, such as the circumferential slot, on the everter end 232. Continued application of force on the everting member 212 in a direction toward the coupler ring 228 causes the posts or pins 230 to pierce through the tissue of the free end region 229a, thereby securing the arterial segment 229 to the coupler ring 228. The expansion ring 216 is retained in its radially expanded condition, rigidly securing the arterial vessel wall to the inner wall of the coupler ring 228, while the everter end 232 of the everting member 212 everted the free end region 229a and impales the free end region 229a on the plurality of posts or pins 230. To facilitate retaining the expansion ring 216 in its radially expanded condition, the inner shaft 228 may be locked in a selected axial location relative to the outer shaft 220, such as with a bayonet-type fitting, a cam, or a threaded locking mechanism.

A vessel clamp (not shown) could be used to grasp the arterial segment 229 just upstream of the coupler ring 228, such that the end cap 222 contacts an inner wall of arterial tissue at a location directly opposite where an outer wall of the arterial tissue is in intimate contact with the vessel clamp (in other words, the end cap 222 comes into contact with arterial tissue abutting the vessel claim), preventing further axial advancement of the end cap 222 and inner shaft 218, such that continued advancement of the everter in the direction of the arterial segment 29 pushes the outer shaft 220 toward the end cap 222, resulting in expansion of the expansion ring 216.

The expansion ring 216 is then permitted to relax, and the everter device 210 is removed. The process is repeated for another arterial segment (not shown) to be coapted to the first arterial segment 229, so as to secure a free end region of that other arterial segment to a mating coupler ring (also not shown), after which the two coupler rings can be brought together to complete the end-to-end microanastomosis.

Figure 24:
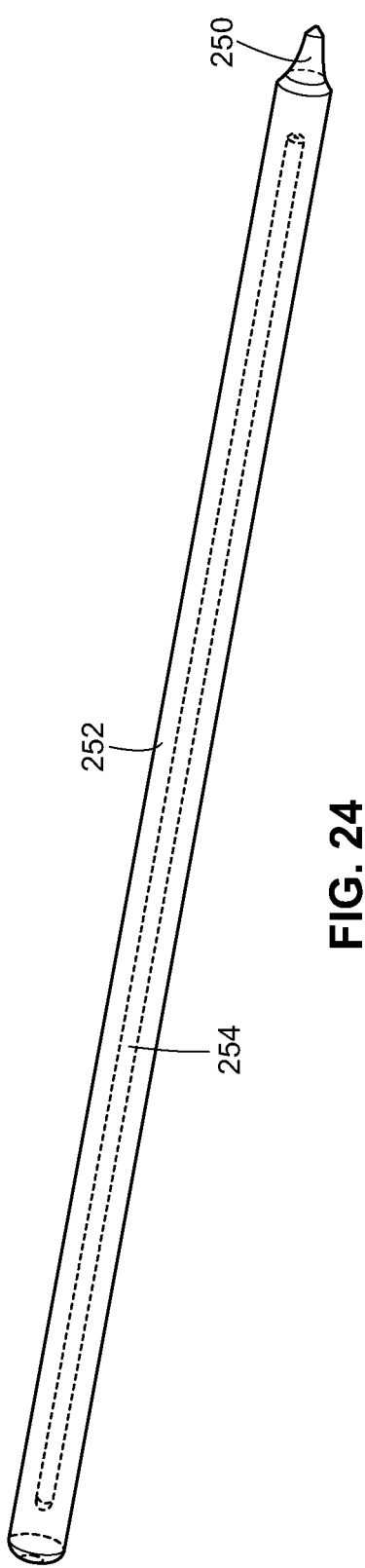
FIG. 24 is a perspective view of a fourth embodiment of an arterial everter device of the present disclosure, including an eversion surface made of a pierceable material at a first end thereof, and the device having a structural support rod therein.
Figure 25:
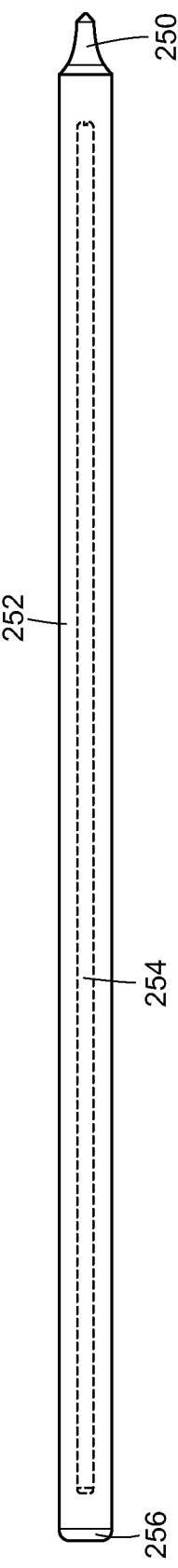
FIG. 25 is a plan view of the arterial everter device of FIG. 24, the device having a structural support rod therein and a second eversion surface at an end opposite the end with the first eversion surface.

Turning to FIGS. 24 and 25, an everter device 252 of a fourth embodiment is provided. According to this embodiment, the everter device 252 includes at least a first eversion surface 250 at a first end thereof, the eversion surface 250 being formed of a pierceable material, such as a medical grade silicone with Shore A hardness between 10 and 50. By forming the eversion surface 250 of a pierceable material, the plurality of coupler posts or pins 130 (see FIG. 12) can pierce through the eversion surface 250 and into the device 252 without having to provide a recess in the everter end, and without causing significant deformation of the coupler pins 130.

The exterior of the everter device 252 may be made substantially or even entirely made of the pierceable material. The device 252 may be provided with a supporting rod 254, such as a stainless steel rod. Other materials besides stainless steel could be utilized for the supporting rod 254, such as a rigid or semi-rigid material like a thermoplastic. Desirably, the supporting rod 254 is made of a material that can support flexible regions of the device 252 while preventing excessive deformation during use. While the supporting rod 254 is shown as being embedded within the device 252, it will be appreciated that the supporting rod 254 may be provided on an exterior of the device 252, or may be partially embedded within the device 252 and partially on the exterior of the device 252.

A tip of the eversion surface 250 may be made out of a flexible material such that when a vessel requires clamping or fixation behind the coupler ring, the tip can deform, thereby minimizing damage to the intima of the vessel.

In addition to an eversion surface 250 at a first end of the device 252, a second eversion surface 256 may be provided at a second, opposite end of the device 252. This second eversion surface 256 may have a different size and/or contour than the first eversion surface 250, increasing the versatility of the device 252 by permitting its use with a greater size range of vessels and couplers with a single eversion device 252.

The device 252 may be deformable by the user, which aids in manipulating the device to a custom shape to facilitate manipulation of the device 252 in small and/or hard to reach anatomical locations.

While various embodiments have been described herein, it will be appreciated that modifications may be made thereto that are still within the scope of the appended claims.

What is claimed is:

1. An everter device comprising:
   an elongate main body having a first end and a second end opposite the first end;
   an eversion surface at the first end of the elongate main body, the eversion surface formed of a pierceable material permitting penetration by coupler pins when everting a portion of a vessel; and
   a supporting rod entirely embedded within the elongate main body.

2. The everter device of claim 1, the pierceable material including a medical grade silicone having a Shore A hardness in a range of 10-50.

3. The everter device of claim 1, wherein the elongate main body is at least substantially formed of the pierceable material.

4. The everter device of claim 1, wherein the supporting rod is a semi-rigid thermoplastic material.

5. The everter device of claim 1, further comprising a second eversion surface at a second end of the eversion device opposite the eversion surface at the first end of the everter device.

6. The everter device of claim 5, the second eversion surface having at least one of a different size or contour than the eversion surface at the first end of the everter device.

7. The everter device of claim 1, the supporting rod terminating proximally of the first end of the elongate main body, a tip of the eversion surface being made of a flexible material that can deform upon contact with the intima of a vessel.

* * * * *